US010342750B2

(12) United States Patent
Prencipe et al.

(10) Patent No.: US 10,342,750 B2
(45) Date of Patent: *Jul. 9, 2019

(54) DENTIFRICE COMPOSITIONS COMPRISING ZINC OXIDE AND ZINC CITRATE

(71) Applicant: Colgate-Palmolive Company, New York, NY (US)

(72) Inventors: Michael Prencipe, Princeton Junction, NJ (US); Yun Xu, Guangzhou (CN); Xiao Yi Huang, Guangzhou (CN); Steven Fisher, Middlesex, NJ (US); Betty Won, New Brunswick, NJ (US); Lyndsay Schaeffer-Korbylo, Flemington, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/106,280

(22) PCT Filed: Dec. 19, 2014

(86) PCT No.: PCT/US2014/071335
§ 371 (c)(1),
(2) Date: Jun. 18, 2016

(87) PCT Pub. No.: WO2015/095627
PCT Pub. Date: Jun. 25, 2015

(65) Prior Publication Data
US 2016/0303010 A1 Oct. 20, 2016

(30) Foreign Application Priority Data
Dec. 19, 2013 (CN) .......................... 2013 1 0701692

(51) Int. Cl.
*A61K 8/27* (2006.01)
*A61K 31/32* (2006.01)
*A61K 8/24* (2006.01)
*A61Q 11/00* (2006.01)

(52) U.S. Cl.
CPC ............... *A61K 8/27* (2013.01); *A61Q 11/00* (2013.01); *A61K 2800/5922* (2013.01)

(58) Field of Classification Search
CPC ... A61K 8/24; A61K 8/19; A61K 8/21; A61K 8/365; A61K 8/27; A61K 2800/30; A61Q 11/00
See application file for complete search history.

(56) References Cited

U.S. PATENT DOCUMENTS

| | | | |
|---|---|---|---|
| 4,469,674 A | 9/1984 | Shah et al. | |
| 5,330,748 A | 7/1994 | Winston et al. | |
| 5,830,437 A * | 11/1998 | Ascione | A61K 8/25 424/49 |
| 6,015,547 A | 1/2000 | Yam | |
| 8,932,563 B2 | 1/2015 | Martinetti et al. | |
| 9,486,396 B2 | 11/2016 | Maloney et al. | |
| 2013/0078197 A1 | 3/2013 | Mello et al. | |
| 2015/0297500 A1* | 10/2015 | Robinson | A61K 8/27 424/401 |

FOREIGN PATENT DOCUMENTS

| | | |
|---|---|---|
| EP | 1072253 | 1/2001 |
| WO | WO 2010/138492 | 12/2010 |
| WO | WO 2010/138547 | 12/2010 |
| WO | WO 2012/087268 | 6/2012 |
| WO | WO 2014/088575 | 6/2014 |
| WO | WO 2014/094225 | 6/2014 |
| WO | WO 2014/100928 | 7/2014 |

OTHER PUBLICATIONS

International Search Report and Written Opinoin mailed in International Application No. PCT/US2014/071335 dated Apr. 15, 2015.
Bilich, 1998, Big Medical Dictionary. Oxford. T.1, Veche-AST, p. 192.
Katz, 2017, "Guide to anaerobic bacteria and mad breath halitosis," http://www.therabreath.com/anaerobic-bacteria.html.

* cited by examiner

*Primary Examiner* — Lezah Roberts

(57) ABSTRACT

Described herein are oral care compositions comprising a combination of zinc oxide and zinc citrate, and methods of preparing and using the same.

9 Claims, No Drawings

DENTIFRICE COMPOSITIONS COMPRISING ZINC OXIDE AND ZINC CITRATE

CROSS-REFERENCE TO RELATED PATENT APPLICATIONS

The present application is a U.S. national stage application under 35 U.S.C. § 371 of PCT Application No. PCT/US2014/071335, filed Dec. 19, 2014 that claims priority to Chinese Patent Application No, 201310701692.8, filed Dec. 19, 2013, the entireties of which are incorporated by reference herein.

BACKGROUND

Soluble zinc salts, such as zinc citrate, have been used in dentifrice compositions. There is a need for agents in oral care products that provide enhanced benefits including antibacterial, anticavity, enamel erosion prevention, breath freshening, and the like. In particular, there is a need for an effective zinc system in dentifrice formulations that has improved antibacterial activity and delivers improved oral biofilm reduction.

BRIEF SUMMARY

In some embodiments, provided is an oral care composition comprising zinc oxide and zinc citrate wherein the weight ratio of zinc oxide:zinc citrate is 1.5:1 to 4.5:1. In other embodiments, the weight ratio is 1.5:1 to 4:1, 1.7:1 to 2.3:1, 1.9:1 to 2.1:1, or about 2:1. Also, the corresponding molar ratios based on these weight ratios can be used.

Some embodiments provide a method of treating or preventing a disease or condition of the oral cavity comprising contacting an oral cavity surface of a patient in need thereof with any one of the compositions described herein.

Also provide is a use of zinc oxide and zinc citrate, wherein the weight ratio of zinc oxide:zinc citrate is 1.5:1 to 4.5:1, in an oral care composition to reduce or inhibit biofilm formation in an oral cavity. In other embodiments, the weight ratio is 1.5:1 to 4:1, 1.7:1 to 2.3:1, 1.9:1 to 2.1:1, or about 2:1. Also, the corresponding molar ratios based on these weight ratios can be used.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

It has been surprisingly and unexpectedly discovered that a specific ratio of zinc oxide to zinc citrate provides a high level of efficacy, e.g., reduction in biofilm in the oral cavity, increased anti-microbial effect, and the like.

In some embodiments, provided is an oral care composition comprising zinc oxide and zinc citrate wherein the weight ratio of zinc oxide to zinc citrate is 1.5:1 to 4.5:1, optionally 1.5:1 to 4:1, 1.7:1 to 2.3:1, 1.9:1 to 2.1:1, or about 2:1 and the amount of zinc oxide is 0.5 to 1.5% and the amount of zinc citrate is 0.25 to 0.75%, by weight of composition. In some embodiments, the amount of zinc oxide is 1% and the amount of zinc citrate is 0.5%. In some embodiments, effectiveness of the inventive ratio of zinc oxide to zinc citrate provides a synergistic anti-microbial and/or anti-oral biofilm effect. In some embodiments, the delivery or uptake of zinc is synergistically increased in an oral cavity soft or hard surface, e.g. a tooth.

The compositions also typically comprise an orally acceptable carrier or vehicle. The carrier may comprise abrasives, thickening agents, humectants, polymers, colorants, viscosity modifiers, foam modulators, emulsifiers, pH modifying agents, diluents, mouth feel agents, sweetening agents, flavor agents, preservatives, suitable cosmetic and/or therapeutic actives, and combinations thereof. It is understood that while general attributes of each of the above categories of materials may differ, there may be some common attributes and any given material may serve multiple purposes within two or more of such categories of materials. All of the ingredients in the compositions may have functions in addition to their primary function, and may contribute to the overall properties of the composition, including its stability, efficacy, consistency, mouthfeel, taste, odor and so forth. Preferably, the carrier is selected for compatibility with other ingredients of the composition.

The specific composition of the carrier preferably depends on the intended use of the composition. In various embodiments, the carrier is aqueous, comprising from 5 to 95%, by weight, water or from 10 to 70%/o, by weight, water. In other embodiments, the carrier is substantially non-aqueous. In a dentifrice carrier, water content can be from 5 to 70%, from 10 to 50%, or from 20 to 40%, by weight.

In some embodiments, the compositions further comprise one or more components selected from a fluoride ion source; a tartar control agent; a buffering agent; an antibacterial agent; an abrasive; and a combination of two or more thereof.

Some embodiments provide compositions wherein at least one of the one or more components is a fluoride ion source selected from: stannous fluoride, sodium fluoride, potassium fluoride, sodium monofluorophosphate, sodium fluorosilicate, ammonium fluorosilicate, amine fluoride, ammonium fluoride, and a combination of two or more thereof.

Other optional additives may be included. Among such optional additives, included are those provided in order to change appearance or aesthetic appeal, and/or to preserve the final product, and/or for taste/cosmetic appeal and/or as therapeutic and prophylactic ingredients for oral health, prevention or treatment of a condition or disorder of hard or soft tissue of the oral cavity, or the prevention or treatment of a physiological disorder or condition.

Some embodiments provide a composition wherein a preservative is present. In some embodiments, the preservative is selected from parabens, potassium sorbate, benzyl alcohol, phenoxyethanol, polyaminopropryl biguanide, caprylic acid, sodium benzoate and cetylpyridinium chloride. In some embodiments, the preservative is present at a concentration of 0.0001 to 1%, by weight.

Colorants such as dyes may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-n-aphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-DELTA-3,5-cycl-ohexadienimine], FD&C Blue No. 1 (disodium salt of dibenzyldiethyl-di-amino-triphenylcarbinol trisulfonic acid anhydrite), FD&C Blue No. 2 (sodium salt of disulfonic acid of indigotin) and mixtures thereof in various proportions. Typically, colorants if included are present in very small quantities.

Flavoring agents include, but are not limited to, natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. These flavoring agents can be used individually or in admixture. Commonly used flavors include mints such as peppermint, artificial vanilla, cinnamon derivatives, and various fruit flavors, whether employed individually or in admixture. Generally, any flavoring agent or food additive, such as those described in Chemicals Used in Food Processing, publication 1274 by the National Academy of Sciences, pages 63-258, may be used. Typically, flavoring agents, if included, are present at a concentration of from 0.01 to 1%, by weight. In some embodiments, the flavoring agent may be present at a concentration of 0.2%, by weight.

Sweeteners include both natural and artificial sweeteners. Suitable sweeteners include water soluble sweetening agents such as monosaccharides, disaccharides and poysaccharides such as xylose, ribose, glucose (dextrose), mannose, galactose, fructose (levulose), sucrose (sugar), maltose, water soluble artificial sweeteners such as the soluble saccharin salts, i.e., sodium or calcium saccharin salts, cyclamate salts dipeptide based sweeteners, such a L-aspartic acid derived sweeteners, such as L-aspartyl-L-phenylalaine methyl ester (aspartame). In general, the effective amount of sweetener is utilized to provide the level of sweetness desired for a particular composition, will vary with the sweetener selected. This amount will normally be from 0.001 to 5%, by weight. In some embodiments, the sweetener is sodium saccharin and is present at a concentration of 0.01%, by weight.

Whitening agents, material which is effective to effect whitening of a tooth surface to which it is applied, such as hydrogen peroxide and urea peroxide, high cleaning silica, preservatives, silicones, and chlorophyll compounds may be incorporated into the compositions. In various embodiments, the compositions comprise a peroxide whitening agent, comprising a peroxide compound. A peroxide compound is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof. In some embodiments, the peroxide compound comprises hydrogen peroxide. In some embodiments, the peroxide compound consists essentially of hydrogen peroxide. In some embodiments a non-peroxide whitening agent may be provided. Whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite. One or more whitening agents are optionally present in a tooth-whitening effective total amount. In some embodiments the whitening agent is separated from the aqueous carrier. In some embodiments the whitening agent is separated from the aqueous carrier by encapsulation of the whitening agent.

Optionally, breath freshening agents may be provided. Any orally acceptable breath freshening agent can be used, including without limitation. One or more breath freshening agents are optionally present in a breath freshening effective total amount.

Other embodiments provide compositions wherein at least one of the one or more components is a tartar control agent. Tartar control agents among those useful herein include phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof, wherein sodium can optionally be replaced by potassium or ammonium. Other useful anticalculus agents include polycarboxylate polymers and polyvinyl methyl ether/maleic anhydride (PVME/MA) copolymers, such as those available under the Gantrez™ brand from ISP, Wayne, N.J. In some embodiments, a phosphate is present at a concentration of from 0.01 to 10%, by weight. In some embodiments, a phosphate is present at a concentration of from 1%, by weight.

Some embodiments provide compositions wherein a buffering agent is present. In some embodiments, sodium phosphate monobasic is present at a concentration of from 0.01 to 5%, by weight. In some embodiments, sodium phosphate monobasic phosphate is present at a concentration of 1%, by weight. In some embodiments, sodium phosphate dibasic is present at a concentration of from 0.01 to 5%, by weight. In some embodiments, sodium phosphate dibasic phosphate is present at a concentration of 0.15%, by weight.

Other optional additives include antimicrobial (e.g., antibacterial) agents. Any orally acceptable antimicrobial agent can be used, including Triclosan (5-chloro-2-(2,4-dichlorophenoxy)phenol); 8-hydroxyquinoline and salts thereof, zinc and stannous ion sources such as zinc citrate, zinc sulphate, zinc glycinate, sodium zinc citrate and stannous pyrophosphate; copper (II) compounds such as copper (I) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethyl-pyridinium chloride); bisguanides, such as chlorhexidine digluconate, hexetidine, octenidine, alexidine; halogenated bisphenolic compounds, such as 2,2' methylenebis-(4-chloro-6-bromophenol); benzalkonium chloride; salicylanilide, domiphen bromide; iodine; sulfonamides; bisbiguanides; phenolics; piperidino derivatives such as delmopinol and octapinol; *magnolia* extract; grapeseed extract; thymol; eugenol; menthol; geraniol; carvacrol; citral; eucalyptol; catechol; 4-allylcatechol; hexyl resorcinol; methyl salicylate; antibiotics such as augmentin, amoxicillin, tetracycline, doxycycline, minocycline, metronidazole, neomycin, kanamycin and clindamycin; and mixtures thereof. A further illustrative list of useful antibacterial agents is provided in U.S. Pat. No. 5,776,435, Gaffar, et al., issued Jul. 7, 1998. In some embodiments, the antimicrobial agent is present at a concentration of from 0.001 to 1%, by weight. In some embodiments, the antimicrobial agent is cetylpyridinium chloride. In some embodiments, cetylpyridinium chloride is present at a concentration of from 0.001 to 1%, by weight. In other embodiments, cetylpyridinium chloride is present at a concentration of 0.05%, by weight.

Antioxidants are another class of optional additives. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

Also optional, a saliva stimulating agent, useful for example in amelioration of dry mouth, may be included. Any orally acceptable saliva stimulating agent can be used, including without limitation food acids such as citric, lactic, malic, succinic, ascorbic, adipic, fumaric, and tartaric acids, and mixtures thereof. One or more saliva stimulating agents are optionally present in a saliva stimulating effective total amount.

Optionally, an antiplaque (e.g., plaque disrupting) agent may be included. Any orally acceptable antiplaque agent can be used, including without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and mixtures thereof.

Optional desensitizing agents include potassium citrate, potassium chloride, potassium tartrate, potassium bicarbonate, potassium oxalate, potassium nitrate, strontium salts, and mixtures thereof.

Optional additives also include vitamins, herbs and proteins. Vitamins include Vitamins C and D, thiamine, riboflavin, calcium pantothenate, niacin, folic acid, nicotinamide, pyridoxine, cyanocobalamin, para-aminobenzoic acid, bioflavonoids, pantheon, retinyl palmitate, tocopherol acetate, and mixtures thereof. Herbs such as *Chamomilla recutita*, *Mentha piperita*, *Salvia officinalis*, and *Commiphora myrrha* may optionally be included. Suitable proteins include milk proteins and enzymes such as peroxide-producing enzymes, amylase, plaque-disrupting agents such as papain, glucoamylase, glucose oxidase, and "next generation" enzymes."

In some embodiments, the composition has a free water content of greater than 10%, by weight. In some embodiments, the composition has a free water content of greater than 11%, by weight. In other embodiments, the composition has a free water content of greater than 12%, by weight. Yet other embodiments provide compositions wherein the free water content is greater than 13%, by weight. Still other embodiments provide compositions having a free water content of greater than 14%, by weight. In some embodiments, the composition has a free water content of greater than 15%, by weight. While other embodiments provide compositions have a free water content of greater than 16%, by weight. In some embodiments, the composition has a free water content of 17%, by weight. In some embodiments, the composition has a free water content of greater than 17%, by weight. In some embodiments, the composition has a free water content of from 10% to 20%, by weight.

In some embodiments, the carrier comprises a humectant, such as glycerin, sorbitol or an alkylene glycol such as polyethylene glycol or propylene glycol. In some embodiments, the carrier comprises a humectant at a level of from 10 to 80% by weight, or 20 to 60% by weight of the composition. Carrier compositions among those useful herein are disclosed in U.S. Pat. No. 5,695,746 to Garlick, Jr., et al. and U.S. Pat. No. 4,839,157 to Mei-King Ng et al.

Thickeners or gelling agents useful herein include inorganic, natural or synthetic thickeners or gelling agents. In some configurations, the carrier comprises the thickener and gelling agent at total levels of from 0.1 to 15% by weight, or from 0.4 to 10% by weight of the composition. Examples of thickeners and gelling agents useful herein include inorganic thickening silicas such as: an amorphous silica, for example Zeodent® 165 (Huber Corporation); Irish moss; iota-carrageenan; gum tragacanth; or polyvinylpyrrolidone.

In certain embodiments, the carrier comprises an abrasive or polishing agent, such as a silica, a calcined alumina, sodium bicarbonate, calcium carbonate, dicalcium phosphate or calcium pyrophosphate. In various embodiments, the carrier is clear. In various embodiments, the carrier comprises an abrasive at a level of from 5 to 70% by weight of the composition.

In some embodiments, the compositions comprise a surfactant or mixture of surfactants. Surfactants among those useful herein include water-soluble salts of at least one higher fatty acid monoglyceride monosulfate, such as the sodium salt of the monsulfated monoglyceride of hydrogenated coconut oil fatty acids; cocamidopropyl betaine; a higher alkyl sulfate such as sodium lauryl sulfate; an alkyl aryl sulfonate such as sodium dodecyl benzene sulfonate; a higher alkyl sulfoacetate; sodium lauryl sulfoacetate; a higher fatty acid ester of 1,2-dihydroxy propane sulfonate;

and a substantially saturated higher aliphatic acyl amides of a lower aliphatic amino carboxylic acid, such as those having 12 to 16 carbons in the fatty acid, alkyl or acyl radicals; and mixtures thereof. Amides can be, for example, N-lauroyl sarcosine, and the sodium, potassium, and ethanolamine salts of N-lauroyl, N-myristoyl, or N-palmitoyl sarcosine. In various embodiments, the surfactant is present at a concentration of from 0.3 to 5% by weight of composition, or 0.5 to 3% by weight of composition.

Provides, in a first embodiment, is an oral composition (Composition 1) comprising for example, an oral care composition comprising zinc oxide and zinc citrate wherein the weight ratio of zinc oxide:zinc citrate is 1.7:1 to 2.3:1, optionally 1.9:1 to 2.1:1, or about 2:1; for example:
1.1. Composition 1 wherein the amount of zinc oxide is 0.5 to 1.5% and the amount of zinc citrate is 0.25 to 0.75%, by weight of composition;
1.2. Composition 1.1 wherein the amount of zinc oxide is 1% and the amount of zinc citrate is 0.5%;
1.3. Any of the foregoing compositions further comprising an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof;
1.4. Any of the foregoing compositions comprising L-arginine in free or orally acceptable salt form;
1.5. Any of the foregoing compositions comprising buffering agents, e.g., sodium phosphate buffer (e.g., sodium phosphate monobasic and disodium phosphate);
1.6. Any of the foregoing compositions comprising a humectant, e.g., selected from glycerin, sorbitol, propylene glycol, polyethylene glycol, xylitol, and mixtures thereof;
1.7. Any of the preceding compositions further comprising an abrasive or particulate;
1.8. The immediately preceding composition wherein the abrasive or particulate is selected from sodium bicarbonate, calcium phosphate (e.g., dicalcium phosphate dihydrate), calcium sulfate, precipitated calcium carbonate, calcium pyrophosphate, silica (e.g., hydrated silica), iron oxide, aluminum oxide, perlite, plastic particles, e.g., polyethylene, and combinations thereof;
1.9. Any of the preceding compositions comprising an abrasive in an amount of 15 wt. % to 70 wt. % of the total composition weight;
1.10. Any of the preceding compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof. e.g. in an amount of from 0.3% to 4.5% by weight;
1.11. Any of the preceding compositions further comprising a viscosity modifying amount of one or more polymers selected from polyethylene glycols, polysaccharides (e.g., cellulose derivatives, for example carboxymethyl cellulose, polysaccharide gums, for example xanthan gum or carrageenan gum), and combinations thereof;
1.12. Any of the preceding compositions in the form of a dentifrice, mouthwash, chewing gum or lozenge;
1.13. Any of the preceding compositions further comprising flavoring, fragrance and/or coloring;
1.14. Any of the preceding compositions further comprising water.
1.15. Any of the foregoing compositions comprising one or more antibacterial agents, for example comprising an antibacterial agent selected from halogenated diphenyl ether (e.g. triclosan), herbal extracts and essential oils (e.g., rosemary extract, tea extract, *magnolia* extract, thymol, menthol, eucalyptol, geraniol, carvacrol, citral, hinokitol, catechol, methyl salicylate, epigallocatechin gallate, epigallocatechin, gallic acid, miswak extract, seabuckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride;
1.16. Any of the preceding compositions further comprising a whitening agent, e.g., a selected from the group consisting of peroxides, metal chlorites, perborates, percarbonates, peroxyacids, hypochlorites, and combinations thereof;
1.17. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);
1.18. Any of the preceding compositions further comprising an agent that interferes with or prevents bacterial attachment, e.g., solbrol or chitosan;
1.19. Any of the preceding compositions further comprising a source of calcium and phosphate selected from (i) calcium-glass complexes, e.g., calcium sodium phosphosilicates, and (ii) calcium-protein complexes, e.g., casein phosphopeptide-amorphous calcium phosphate;
1.20. Any of the preceding compositions further comprising a soluble calcium salt, e.g., selected from calcium sulfate, calcium chloride, calcium nitrate, calcium acetate, calcium lactate, and combinations thereof;
1.21. Any of the preceding compositions further comprising a physiologically or orally acceptable potassium salt, e.g., potassium nitrate or potassium chloride, in an amount effective to reduce dentinal sensitivity;
1.22. Any of the preceding compositions further comprising a breath freshener, fragrance or flavoring;
1.23. Any of the preceding compositions effective upon application to the oral cavity. e.g., with brushing, to (i) reduce hypersensitivity of the teeth, (ii) to reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; and/or (xv) promote systemic health, including cardiovascular health, e.g., by reducing potential for systemic infection via the oral tissues:

1.24. A composition obtained or obtainable by combining the ingredients as set forth in any of the preceding compositions;

1.25. Any of the preceding compositions wherein the composition is a toothpaste or mouthwash optionally further comprising one or more of one or more of water, abrasives, surfactants, foaming agents, vitamins, polymers, enzymes, humectants, thickeners, antimicrobial agents, preservatives, flavorings, colorings and/or combinations thereof;

1.26. Any of the preceding compositions wherein the composition is toothpaste.

In some embodiments, the zinc oxide and zinc citrate are not contained in a film. In some embodiments, the zinc oxide and zinc citrate are in a single phase.

Some embodiments provide a method of treating or preventing a disease or condition of the oral cavity comprising contacting an oral cavity surface of a patient in need thereof with any one of the compositions described herein. In other embodiments, the disease or condition of the oral cavity is halitosis. In some embodiments, provided is a method of reducing volatile sulfur compounds in the oral cavity of a subject in need thereof. In further embodiments, provided is a method for increasing the delivery of a metal ion to an oral cavity surface.

In certain embodiments, the compositions described herein can be used, for example, for cavity prevention, whitening, plaque prevention or reduction, gingivitis prevention or reduction, tartar control, breath malodor prevention or reduction, and stain prevention.

Examples of suitable product forms for compositions include dentifrices, mouthwashes, chewing gums and lozenges.

A type of product form is a dentifrice. The term "dentifrice" generally denotes formulations which are used to clean the surfaces of the oral cavity. The dentifrice is an oral composition that is not intentionally swallowed for purposes of systemic administration of therapeutic agents, but is applied to the oral cavity, used to treat the oral cavity and then expectorated. Typically the dentifrice is used in conjunction with a cleaning implement such as a toothbrush, usually by applying it to the bristles of the toothbrush and then brushing the accessible surfaces of the oral cavity. Preferably the dentifrice is in the form of a paste or a gel (or a combination thereof).

Another type of product form is a mouthwash. The term "mouthwash" generally denotes liquid formulations which are used to rinse the surfaces of the oral cavity and provide the user with a sensation of oral cleanliness and refreshment. The mouthwash is an oral composition that is not intentionally swallowed for purposes of systemic administration of therapeutic agents, but is applied to the oral cavity, used to treat the oral cavity and then expectorated. A mouthwash composition will usually contain an aqueous continuous phase. The amount of water generally ranges from 70 to 99% by weight based on the total weight of the mouthwash.

Compositions as described herein can be prepared according to methods readily known to those skilled in the art.

Embodiments of the present invention are further described in the following examples. The examples are merely illustrative and do not in any way limit the scope of the invention as described and claimed.

EXAMPLES

Example 1

Formulas with different amounts and ratios of zinc oxide and zinc citrate were tested in a standard toothpaste formulation using an assay based on the metabolic indicator dye, resazurin to assess bacterial viability following treatment. A five species mix of representative oral species is used in this assay (*Actinomvces viscosus, Lactobacillus casei, Streptococcus oralis, Fusobacterium nucleatum* and *Veillonella parvula*) and treated at a final concentration of 1:100 dentifrice. Bacteria are incubated with test solutions for 1 h prior to staining with 50 µg/ml resazurin solution. When viable bacteria are incubated with resazurin, the blue, non-fluorescent dye is reduced by the bacteria to the pink fluorescent dye resorufin. Fluorescence of test samples is read at 560 nm excitation/590 nm emission and compared to the fluorescence of standardized mixes of live and dead bacteria to determine the percentage of the initial population that remained viable following treatment. The results are in Table 1.

TABLE 1

| Formulation | Percent viable population |
| --- | --- |
| 0% ZnO/0% ZnCitrate | 21.9 |
| 0.5% ZnO/0.5% ZnCitrate | 17.88 |
| 1% ZnO/0.5% ZnCitrate | 12.64 |
| 2% ZnO/0.5% ZnCitrate | 14.32 |
| 3% ZnO/0.5% ZnCitrate | 13.33 |

The results in Table 1 show that at a ratio of 2:1 for zinc oxide:zinc citrate, there were less viable populations. This result is even better than the two formulations having a higher total concentration of zinc.

In the Example below, the experimental methodology used was the Biofilm Growth Inhibition University of Manchester Model. The protocol for this model is as follows:

(1) Dental plaque was collected from four healthy volunteers and pooled together as inoculum. The Optical Density of the inoculum was matched to 0.3 absorbance at 610 nm (2) Sterile hydroxyapatite (HAP) disks were incubated under anaerobic conditions at 37° C. for 24 hours with 1 mL of sterile artificial saliva (with 0.01 weight % sucrose) and 1 mL of pooled saliva in a 24 well microplate.

(3) For each test dentifrice (and for each control) a treatment solution of 1 part dentifrice: 2 parts sterile distilled water by weight was made up. Each freshly prepared treatment solution was added to three wells and allowed to contact the HAP disk therein for 10 minutes.

(4) The liquid phase of each well was then removed and was replaced by 2 mL sterile artificial saliva.

(5) The disks were then maintained at 37° C. under anaerobic conditions for 8 days.

(6) At intervals of 2, 4 and 8 days, the disks were collected aseptically and transferred to half-strength pre-reduced thioglycollate medium (4.5 ml per disk).

(7) 100 μL of the dilution 10-4, 10-5 and 10-6 were plated in duplicates for each disk on Neomycin/Vancomycin (NV) Agar for Total Gram-negative Anaerobes.

(8) The plates were surface-spread using a sterile spreader and were incubated anaerobically at 37° C. for 72 hours, after which time the number of colonies on each plate was counted.

The log 10 CFU/ml (where CFU=colony forming units) for each test dentifrice or control was calculated. A lower Log 10 CFU/ml indicates that the dentifrice tested has greater efficacy in inhibiting biofilm growth.

Example 2

The results obtained using the Biofilm Growth Inhibition University of Manchester Model methodology (above) are shown in Table 2, with the average log 10 CFU/ml obtained from the disk incubated for 8 days in step 6 of the method.

TABLE 2

| No. | Formula | Avg. log10 CFU/ml |
|---|---|---|
| 1 | 0% ZnO, 3.08% ZnCit | 5.72 |
| 2 | 0.67% ZnO, 1.35% ZnCit | 5.29 |
| 3 | 0.86% ZnO, 0.86% ZnCit | 4.94 |
| 4 | 1% ZnO, 0.5% ZnCit | 4.57 |
| 5 | 1.09% ZnO, 0.27% ZnCit | 4.69 |
| 6 | 1.2% ZnO, 0% ZnCit | 5.03 |
| 7 | Placebo | 7.21 |

What is claimed is:

1. An oral care composition having synergistic zinc antibacterial effects comprising zinc oxide and zinc citrate wherein the amount of zinc citrate is about 0.5% by weight of the composition, and the amount of zinc oxide is about 1% by weight of the composition, and wherein the composition comprises a fluoride source selected from stannous fluoride, sodium fluoride, potassium fluoride, sodium fluorosilicate, ammonium fluorosilicate, amine fluoride, ammonium fluoride, titanium fluoride, and combinations thereof, and excludes any other fluoride source, wherein the antibacterial effects are measured as reduction in colony forming units after the composition is applied to incubated hydroxyapatite disks and incubated for 8 days, and wherein the antibacterial effects are measured after said hydroxyapatite disks are collected aseptically and transferred to a half-strength, pre-reduced, thioglycollate medium.

2. The composition of claim 1, further comprising an orally acceptable carrier.

3. The composition of claim 1, wherein the composition is in the form of a dentifrice.

4. The composition of claim 1 wherein the composition is in the form of a toothpaste or tooth gel.

5. The composition of claim 1, wherein the composition comprises greater than 15%, by weight, free water.

6. A method of treating or preventing a disease or condition of the oral cavity comprising contacting an oral cavity surface of a patient in need thereof with the composition of claim 1.

7. The method of claim 6, wherein the disease or condition of the oral cavity is halitosis.

8. A method of reducing or inhibiting biofilm formation in an oral cavity comprising applying a composition of claim 1.

9. The composition of claim 1, wherein the fluoride source is selected from stannous fluoride, sodium fluoride, and combinations thereof.

* * * * *